US006632189B1

(12) United States Patent
Fallen et al.

(10) Patent No.: US 6,632,189 B1
(45) Date of Patent: Oct. 14, 2003

(54) SUPPORT DEVICE FOR SURGICAL SYSTEMS

(75) Inventors: David M. Fallen, Asheville, NC (US); Stuart G. Long, Lake Forest, CA (US); Alphonse Martinet, Placentia, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/390,381

(22) Filed: Sep. 3, 1999

Related U.S. Application Data

(60) Provisional application No. 60/100,852, filed on Sep. 18, 1998.

(51) Int. Cl.[7] .......................... A61M 37/00; B65D 83/10
(52) U.S. Cl. ...................................... 604/4.01; 206/363
(58) Field of Search ............................. 604/6.01, 4.01, 604/7, 153; 422/45; 210/90, 252, 259, 260, 645–47; 417/395; 206/363

(56) References Cited

U.S. PATENT DOCUMENTS

| | | | |
|---|---|---|---|
| 3,709,222 A | | 1/1973 | DeVries |
| 3,881,990 A | * | 5/1975 | Burton et al. ................. 435/1.2 |
| 3,890,969 A | | 6/1975 | Fischel ......................... 128/214 |
| 4,436,620 A | * | 3/1984 | Bellotti et al. ............ 210/321.8 |
| 4,479,761 A | | 10/1984 | Bilstad et al. ............... 417/395 |
| 4,479,762 A | * | 10/1984 | Bilstad et al. ............... 206/364 |
| 4,481,946 A | | 11/1984 | Altshuler et al. ............... 604/4 |
| 4,526,515 A | | 7/1985 | DeVries ......................... 417/63 |
| 4,540,399 A | | 9/1985 | Litzie et al. ..................... 607/4 |
| 4,610,656 A | * | 9/1986 | Mortensen ............. 128/DIG. 3 |
| RE32,303 E | | 12/1986 | Lasker et al. ................... 604/29 |
| 4,704,203 A | | 11/1987 | Reed ........................... 210/188 |
| 4,795,429 A | | 1/1989 | Feldstein |
| 5,011,469 A | | 4/1991 | Buckberg et al. ............... 604/4 |
| 5,062,774 A | * | 11/1991 | Kramer et al. ........ 128/DIG. 12 |
| 5,170,817 A | | 12/1992 | Sunderland |
| 5,375,717 A | | 12/1994 | Roshdy |
| 5,429,058 A | | 7/1995 | Miller |
| 5,496,303 A | | 3/1996 | Antonetti |
| 5,540,653 A | * | 7/1996 | Schock et al. .................. 604/7 |
| 5,573,526 A | | 11/1996 | Hess ........................... 604/408 |
| 5,584,804 A | | 12/1996 | Klatz et al. .................... 604/24 |
| 5,588,816 A | * | 12/1996 | Abbott et al. ................ 417/479 |
| 5,891,080 A | * | 4/1999 | Skinkle et al. ............. 604/6.11 |

FOREIGN PATENT DOCUMENTS

| | | |
|---|---|---|
| EP | 0611227 | 8/1994 |
| GB | 2021418 | 12/1979 |

* cited by examiner

*Primary Examiner*—Angela D. Sykes
*Assistant Examiner*—Leslie Deak
(74) *Attorney, Agent, or Firm*—John Christopher James; Guy L. Cumberbatch

(57) ABSTRACT

A device for supporting and displaying interrelated medical components, such as cardiopulmonary bypass circuit components. The device includes a rigid or flexible chassis having openings therein for receiving the components. A plurality of retainers, such as straps, hooks, or tabs, are provided adjacent the openings for releasably securing the components therein. The chassis may be formed of a thin, flexible polymer sheet having tabs cut therein and adapted to be bent out of the plane of the sheet for securely retaining the various components. The pre-arrangement of the components in close proximity greatly simplifies the task of setting up a particular medical circuit, and reduces the potential for error. For cardiopulmonary bypass circuits, the support device enables the tubing lengths to be reduced, thus reducing the prime volume of the circuit. The chassis is provided with apertures for mounting on rods in the operating room, which rods may extend from the operating table. Handles are also provided on the chassis for conveniently transporting the components or circuit. The compact nature of the chassis and components thereon simplifies and reduces the cost of packaging and shipping. In addition, disposal of a used circuit is facilitated by the provision of a clean bag around the entire system. A pumpless cardioplegia delivery system is also provided.

24 Claims, 13 Drawing Sheets

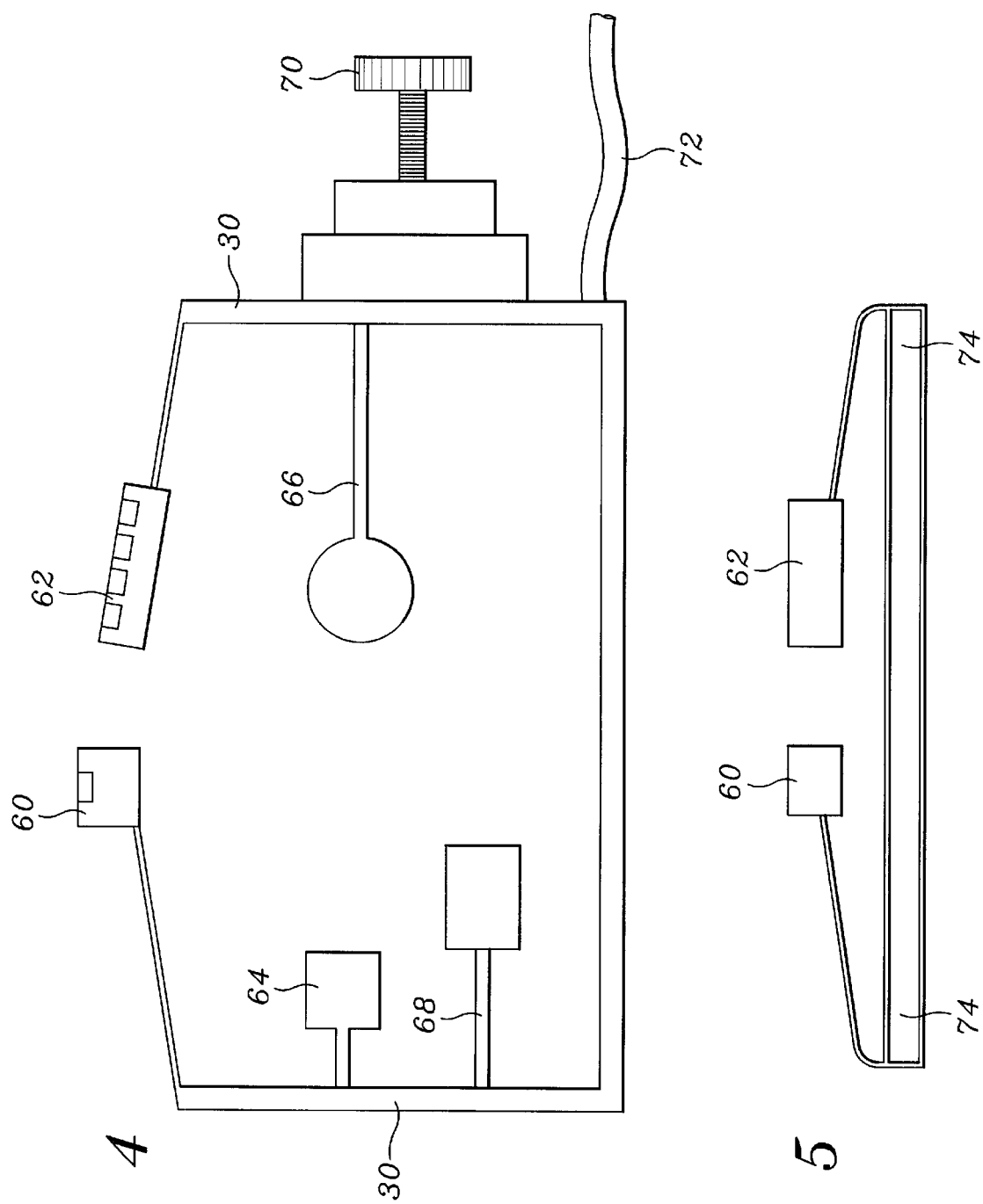

SUPPORT DEVICE FOR SURGICAL SYSTEMS

RELATED APPLICATION

The present application claims the benefit of priority under 35 U.S.C. section 119 (e) from provisional application serial No. 60/100,852, filed Sep. 18, 1998, entitled "SYSTEMS AND METHODS FOR PERFORMING EXTRACORPOREAL BYPASS PROCEDURES".

FIELD OF THE INVENTION

The present invention relates to devices and methods for supporting operating room systems and, more typically, to devices and methods for supporting surgical circuits in a convenient and easily accessible format. The invention is particularly well-suited to enable pre-assembling of cardiopulmonary bypass circuits.

BACKGROUND OF THE INVENTION

Effective circulation and control of the patient's blood are essential to successful heart surgery. This is of particular importance in procedures where the patient is on cardiopulmonary bypass for a significant period of time during surgery. In most modern bypass procedures, blood is oxygenated, treated, and recirculated through the patient by establishing an extracorporeal cardiopulmonary bypass (CPB) circuit in which the blood is mechanically forced by a blood pump through a variety of processing or blood modifying components. A plurality of blood pumps are typically used throughout the CPB circuit to direct the flow of blood through the various CPB circuit components. Generally, the CPB circuit removes blood from the patient, oxygenates the blood, and then returns the blood to the patient. Critics of heart surgery techniques cite a number of drawbacks for procedures that rely on known extracorporeal bypass platforms or circuits.

One well-known drawback of current CPB circuits is the hemolytic effect the multiple mechanical pumps and other instruments in the circuit may have on the blood. For example, a CPB circuit has as many as six pumps for arterial delivery, cardioplegia delivery, cardiotomy suction, left ventricular or aortic root venting, assisted venous drainage, and hemoconcentration. These pumps are typically occlusive roller-type pumps which sequentially pinch and release tubing to affect the desired flow.

Another drawback with current CPB circuits is the potential for detrimental, blood/air interfaces in the long segments of tubing used for cardiotomy suction and venting. Any time blood and air meet and are transported through tubing together, foaming may occur. This foaming results in destruction of clotting factors contained in whole diluted blood circulated through the CPB circuit. This, in turn, results in the release of substances that initiate a cascade of events leading to further dysfunction of platelets, proteins, and eventually organ function in the form of an inflammatory response.

A further drawback of known CPB circuits and procedures is the extended amount of time required by a cardiac perfusionist to set up the circuit prior to performing the procedure. The components of a bypass circuit are typically individually packaged, free-standing units which need to be connected together prior to each surgical procedure. Specifically, the circuit elements must first be located, assembled, and attached to appropriate sterilized circuit tubing. Then, the entire circuit must be flushed out with an inert gas and then primed with a biocompatible fluid, such as blood or saline. The time expenditure increases the cost associated with such surgeries.

Additionally, perfusionists preferably use long lengths of tubing between components to allow for the exchange of bypass components should one of them fail. Furthermore, long lengths of tubing are required to connect venting cannulas and suction tips located in the operative field to blood pumps which then propel the patient's blood to the cardiotomy reservoir for processing and return to the patient. The excess tubing creates excess tubing volume that must be accounted for by using additional blood or saline when the system is being primed. However, it is in the patient's best interest to retain the maximum volume of blood within the body, and excessive dilution of the blood can be harmful. Therefore, the need of the perfusionist for long tubing lengths may not be in the best interest of the patient.

Because of the drawbacks associated with conventional CPB circuits, there is a need for improved methods and apparatuses for performing extracorporeal bypass procedures. In particular, there is a need for an improved CPB circuit that reduces trauma to the blood being processed, reduces the time spent by a perfusionist during setup, provides for reliable access to the vasculature, minimizes the risk of infection to the patient by reducing the number of handmade connections required during assembly and setup, and desirably requires only minor modifications to present procedures.

SUMMARY OF THE INVENTION

The present invention also provides improved systems, methods, and kits for creating and establishing a bypass circuit for use in a variety of extracorporeal procedures such as cardiopulmonary bypass and the like. The improved system of the present invention advantageously allows a user to assemble the system prior to the bypass procedure with minimal setup time. In particular, the present invention provides methods and apparatuses that combine the advantages of putting a patient on cardiopulmonary bypass with the advantages of reduced blood damage (e.g., minimal hemodilution, minimal hemolysis, and preservation of clotting factors).

A further aspect of the present invention is a system provided in a package that can be adapted to use traditional bypass circuit components. The system preferably reduces the total amount of blood and foreign surface contact, thus reducing the potential for foaming which may destroy clotting factors in the blood. Although the present invention provides advantages in the context of practically all bypass procedures, the invention finds particular use with minimally invasive surgical techniques to minimize patient trauma due to surgery and post-operative effects related to blood bypass.

The present invention also lends itself well in the role of a backup support system for "beating heart" coronary artery bypass procedures known by the acronyms OP-CAB or MID-CAB. These procedures utilize extracorporeal bypass support only in the event of patient instability. The circuit is made available in the operating room, but may not be used. This requires the perfusionist to set up the pump system and dedicate a bypass system prior to the patient need in the event bypass is required, which increases the cost dramatically. Alternatively, the components are made available, and the perfusionist must rapidly connect them into a working system under great pressure. The latter solution increases the patient risk and stress on the medical personnel. In contrast, the present invention permits the entire circuit to be made available in the operating room to be ready at a moments notice, but still remain in the original packaging so that if it is not needed, it is not expended.

In one aspect, the present invention provides a support device for surgical systems including a chassis adapted to support and display in a predetermined arrangement a plurality of interrelated surgical system components. The chassis may comprise a generally planar body having a plurality of openings therein for supporting and displaying the surgical system components. Preferably, the planar body is flexible and includes a plurality of tabs formed by cuts therein. The tabs are bendable from the plane of the planar body and are adapted to releasably retain the surgical system components.

In another aspect, the present invention provides a pre-assembled surgical system comprising a plurality of interrelated surgical system components and a chassis. The surgical system components are supported and displayed by the chassis in a predetermined arrangement. If the surgical system is a circuit, such as cardiopulmonary bypass circuit, the system further includes a plurality of tubes for interconnecting the system components. At least some of the tubes are initially disconnected in the pre-assembled system. The chassis desirably includes a plurality of openings for receiving the surgical system components, and a plurality of retainers provided on the chassis adjacent the openings for retaining the components in the openings.

In a further aspect, a method of setting up a cardiopulmonary bypass circuit is provided by the present invention. The method includes a pre-assembled cardiopulmonary bypass circuit including a plurality of bypass components supported and displayed on a chassis. A plurality of tubes interconnect the bypass circuit components, at least some of the tubes initially being disconnected in the pre-assembled bypass circuit. The method includes interconnecting the bypass circuit components using the tubing.

In a still further aspect, a method of disposing of a surgical circuit is disclosed by present invention. The method includes depositing a chassis having a plurality of used components mounted thereon in a clean bag, and transporting the bag to an infectious waste disposal container.

According to a further aspect of the present invention, an apparatus for use in an extracorporeal bypass procedure comprises a cassette or chassis adapted to have a plurality of mounting elements on which a plurality of bypass components can be affixed. The chassis may be molded from generally strong, lightweight surgical grade materials such as plastic, polymers, and the like. The chassis, which is generally rectangular in shape, will preferably be oriented vertically during use. It should be understood, however, that the chassis may be of different configurations and/or may be adapted for use in other orientations. The chassis will preferably allow the bypass circuit to be primed with less than 1000 cc of fluid, preferably about 800 cc of fluid.

The chassis of the present invention will preferably include a plurality of mounting elements, such as recesses, to which the bypass components can be affixed. If recesses are used, the bypass components are fitted within the recesses. The recesses generally allow for at least partial insertion of the component into the chassis so that some portion of the component remains outside the chassis. This facilitates visual inspection of the operation of these components and also allows for handling, de-airing, and replacement of components as desired. The mounting elements on the chassis allow bypass components to be vertically stacked or otherwise arranged to promote the shortest connections between components and also provide cascading or gravity-assisted flow of fluid. Additionally, the use of the chassis further reduces space occupied by equipment in an already crowded surgical environment.

Channels molded into the chassis may be provided to facilitate the connection of components. The chassis may also come as a pre-assembled bypass circuit with bypass components such as the venous reservoir and tubing integrally molded or formed within the chassis. Problems related to the sterilization process, such as heat-kinked lines or component shifting during transportation, will be greatly reduced or eliminated through the use of the chassis according to the present invention. The chassis may come pre-sterilized, assembled, and pre-connected to comprise a priming circuit or loop, thus reducing setup time from a traditional 20–40 minutes down to about 10 minutes or less, and more preferably about 5 minutes. This is particularly advantageous when rapid set-up of a CPB circuit may be needed to support "beating heart" procedures.

According to a further aspect of the present invention, an apparatus for use in extracorporeal procedures comprises a blood circuit defining a flow path having at least one inlet from which blood arrives from the patient, and at least one outlet where oxygenated blood is return to the patient. The flow path is coupled to least one vacuum source adapted to remove blood from the patient. The flow path may contain a plurality of actuatable occluders to control positive and negative pressures between specific components coupled together by the flow path.

In one aspect, the flow path comprises a plurality of inlet lines leading from the patient to a cardiotomy reservoir and a venous line leading from the patient to a venous reservoir. The cardiotomy reservoir, in turn, may be coupled to the venous reservoir as desired. In this embodiment, the venous reservoir is fluidly coupled to an arterial pump which is coupled to an oxygenator. The output of the oxygenator is typically forked to have an arterial line and cardioplegia line both leading to the patient. An arterial filter and an air detector device may be located along the arterial line. An additional pump and a cardioplegia heat exchanger may optionally be located within the cardioplegia line. Preferably, a one-way valve (retroguard) is located between the venous reservoir and the arterial pump to prevent undesired back flow. Additionally, flows to the cardiotomy reservoir and the venous reservoir are preferably independently controlled by vacuum sources. By using a vacuum source instead of pumps, the level of hemolysis over the course of a surgery may be reduced.

A further understanding of the nature advantages of the invention will become apparent by reference to the remaining portions of the specification and drawings.

BRIEF DESCRIPTION OF THE DRAWINGS

FIG. 4 is an elevational view of an exemplary bracket for use with the component support device of the present invention;

FIG. 5 is a top plan view of the bracket of FIG. 4;

DESCRIPTION OF THE PREFERRED EMBODIMENTS

The present invention is related to improved methods, apparatuses, and kits for supporting a number of interconnected, or related, medical components in a convenient and easily accessible manner. In particular, a component support device is disclosed on which a plurality of related medical components may be mounted in close proximity. The support device is especially useful for mounting components in a medical circuit, such as a cardiopulmonary bypass (CPB) circuit as illustrated. However, the support device is also useful for mounting components in other circuits, such as for dialysis. Moreover, the support device is useful for mounting unconnected but related medical components used in a single medical procedure. Therefore, the inventive aspects described herein should not be construed as applicable only in the context of CPB circuits, or circuits in general.

In the context of CPB circuits, the present invention may be adapted to use a variety of safety devices such as arterial line air detection, venous reservoir level detection, over pressure alert/alarm systems, an arterial line retrograde flow prevention valve, and vacuum relief valves for all vent and cardiotomy section lines. In other words, the various components shown in described herein should not be construed as the only type of components which can be conveniently mounted on the support device of the present invention. Furthermore, the specific mounting features of the support device useful for mounting the specific components shown could be modified to mount other components of the same type. For example, the mounting features for the particular oxygenator or reservoir shown could be modified to receive other oxygenators or reservoirs.

The terms "cassette," "frame," or "chassis," and other such terms are all used interchangeably herein to refer to any component support devices having the properties of supporting and displaying surgical components in a secure and convenient manner. For example, the chassis may be a backing plate having recessed cavities or openings in which devices may be press-fit. Alternatively, the chassis may be an enclosure, cassette, or housing of some type in which the medical components are internally mounted. The chassis may itself be coupled to a mounting bracket or other similar device to facilitate positioning within the operating theater. Alternatively, the chassis may be a wire grid or slat-like frame to which the medical components may be attached by tying, or otherwise connecting them.

Figure 1:
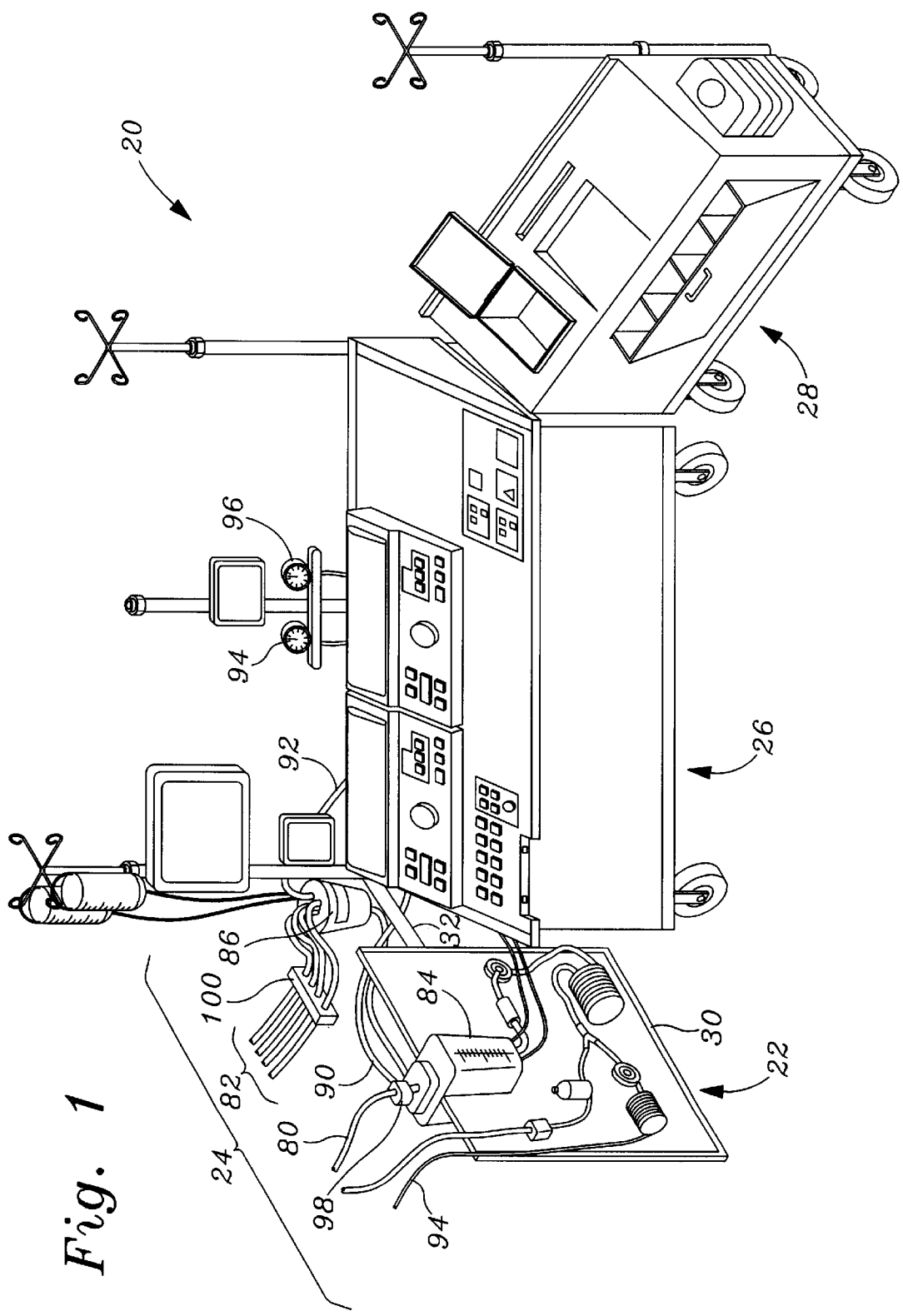
FIG. 1 is a perspective view of a cardiopulmonary bypass system including a component support device of the present invention.

Referring to FIG. 1, one embodiment of a CPB system 20 of the present invention includes a cassette or chassis 22 containing components of an exemplary bypass circuit 24. The system 20 also includes a control workstation 26 and an accessory workstation 28 to provide required operational support elements and accessories for the components of the bypass circuit 24 in the chassis 22. In other embodiments, these workstations may be combined to further reduce the size occupied by the system 20.

Figure 2:
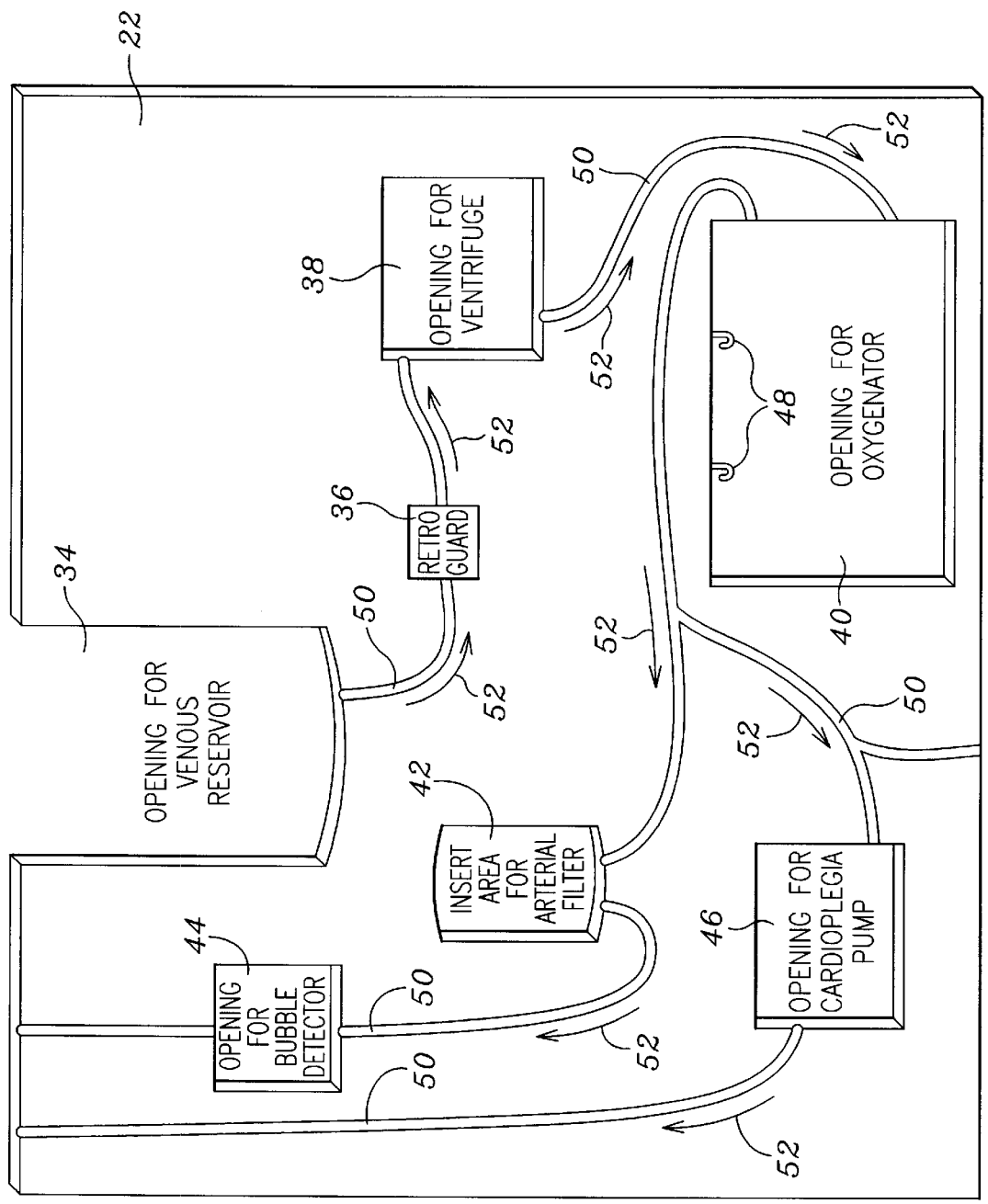
FIG. 2 is a perspective view of one embodiment of a component support device of the present invention.

Referring now to FIGS. 1 and 2, the chassis 22 is typically constructed from strong, lightweight materials such as plastic, fiberglass, or other similar expedient. As seen in FIG. 2, the chassis 22 is mounted in a bracket 30 which slidably receives the chassis and positions it near the control workstation 26. It should be understood that the bracket 30 may be coupled to the chassis 22 using other techniques such as hooks, clips, or similar connectors. The bracket 30 may also be integrally formed with the chassis 22 and mounted to the control workstation 26 via arm 32. In a further embodiment, the chassis 22 may be adapted for mounting on the operating table to minimize tubing lengths required to bring and return blood between the bypass circuit 24 and the patient. The chassis 22 may initially be mounted near the control workstation 26 to prepare the bypass circuit 24, and then may be hooked onto the side, or on another location, of the operating table once bypass is desired. As the only connections between the chassis 22 and control workstation 26 are typically just electrical and vacuum lines, such lines can be easily extended as desired without significantly effecting the operation of the system 20.

Referring again to FIG. 2, in one embodiment the chassis 22 is a molded frame or template having a plurality of openings, recesses, and channels to hold individual components of the bypass circuit 24. It should be understood that the location of components or component openings in the chassis 22 may be configured in many different ways to suit the needs of a particular surgical situation, or medical circuit. Preferably, the openings or components of the chassis 22 will be located to minimize tubing lengths used, reduce floor space occupied by the bypass components, and minimize stagnant flow in the bypass circuit 24. The openings also act as an assembly template so that the risk of errors during assembly is reduced. The recesses and openings further minimize manufacturing problems such as heat-kinked lines during sterilization or component shifting during transportation, because the chassis 22 will effectively secure the components relative to one other. In other words, the spacing between the components is maintained at all times such that the tubing lines are minimized and extend directly without kinking between the components.

Due to the optimum and constant spacing between components, the prime volume for a bypass circuit 24 using the chassis 22 is minimized. In one preferred embodiment, the prime volume is about 800 cubic centimeters (cc), significantly lower than the prime volume in conventional systems.

The chassis 22, as shown in FIG. 2, has an opening 34 for a venous reservoir, an opening 38 for an arterial pump, an opening 40 for an oxygenator, an opening 42 for an arterial filter, an opening 44 for a bubble or air detector, and an optional opening 46 for a cardioplegia pump. The openings may contain mounting elements such as hooks 48, or may be designed to be recesses into which components can be press fit. The openings may also contain connecting elements such as hook and loop fasteners, adhesives, and the like to secure components to the chassis 22. A plurality of channels 50 help define a flow path between components as indicated by arrows 52. The chassis 22 of FIG. 2 is optionally disposable once the bypass components have been removed. In a preferred embodiment, however, as explained below, the entire assembly of the chassis 22 and the bypass components mounted thereon is disposable as a unit.

Figure 3:
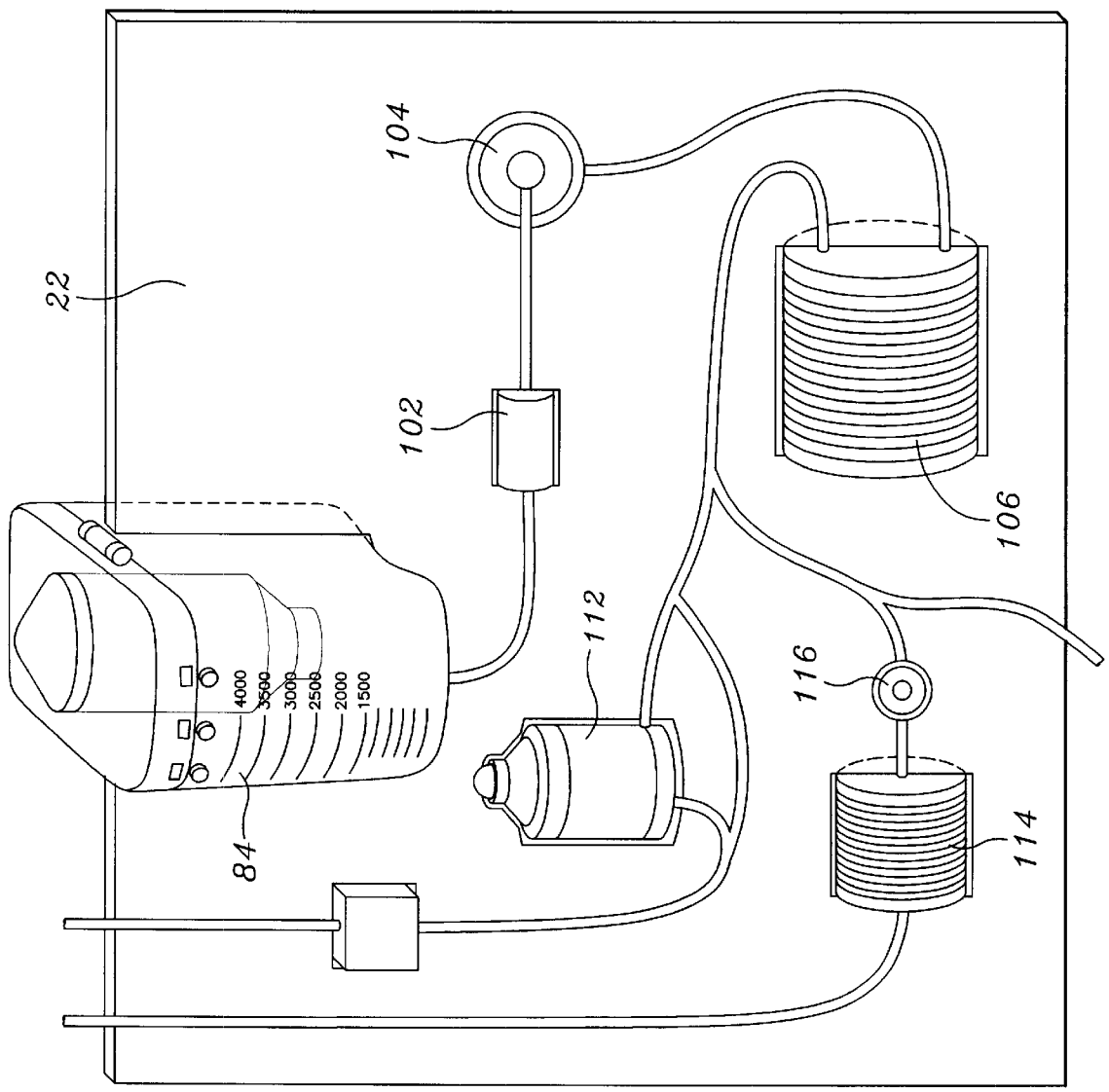
FIG. 3 is a perspective view of another embodiment of a component support device of the present invention and exemplary CPB components supported thereby.

As seen in FIG. 3, the bypass components may also be integrally formed into the chassis 22. This further simplifies set up of the bypass circuit 24 since many of the desired components are prepackaged when removed from the box. Integrally forming the chassis 22 and the bypass components also provides certain cost efficiencies because some components, such as various reservoirs, do not need to be separately molded. The integrated configuration of FIG. 3 may also eliminate the need for polyvinyl chloride (PVC) tubing along most of the fluid pathway, except for using tubing and quick disconnects to couple certain components to the bypass circuit 24.

With reference to FIGS. 4 and 5, the bracket 30 used to support the chassis 22 may also contain elements used in the bypass circuit 24. For example, the bracket 30 of FIG. 4 includes a venous occluder 60 and pinch clamp assembly 62 used to regulate flow into portions of the bypass circuit 24 in the chassis 22 when using various vacuum sources for blood drainage. In some embodiments, the bracket 30 may also have a support 64 for an air detector, a support 66 for a centrifuigal driver, and a support 68 for a cardioplegia pump. Specifically, these certain elements on the chassis 22 will be remotely driven by a driver or motor mounted on the bracket. For example, if a cardioplegia pump is utilized, it will be remotely driven and the roller pump head or centrifugal pump driver assembly will be mounted on the bracket 30. To attach the bracket 30 to the control workstation 26, connectors 70 and wire harnesses 72 are provided with the bracket. As seen in the top view of FIG. 5, slots 74 defined by the bracket 30 slidably receive the chassis 22.

Figure 6:
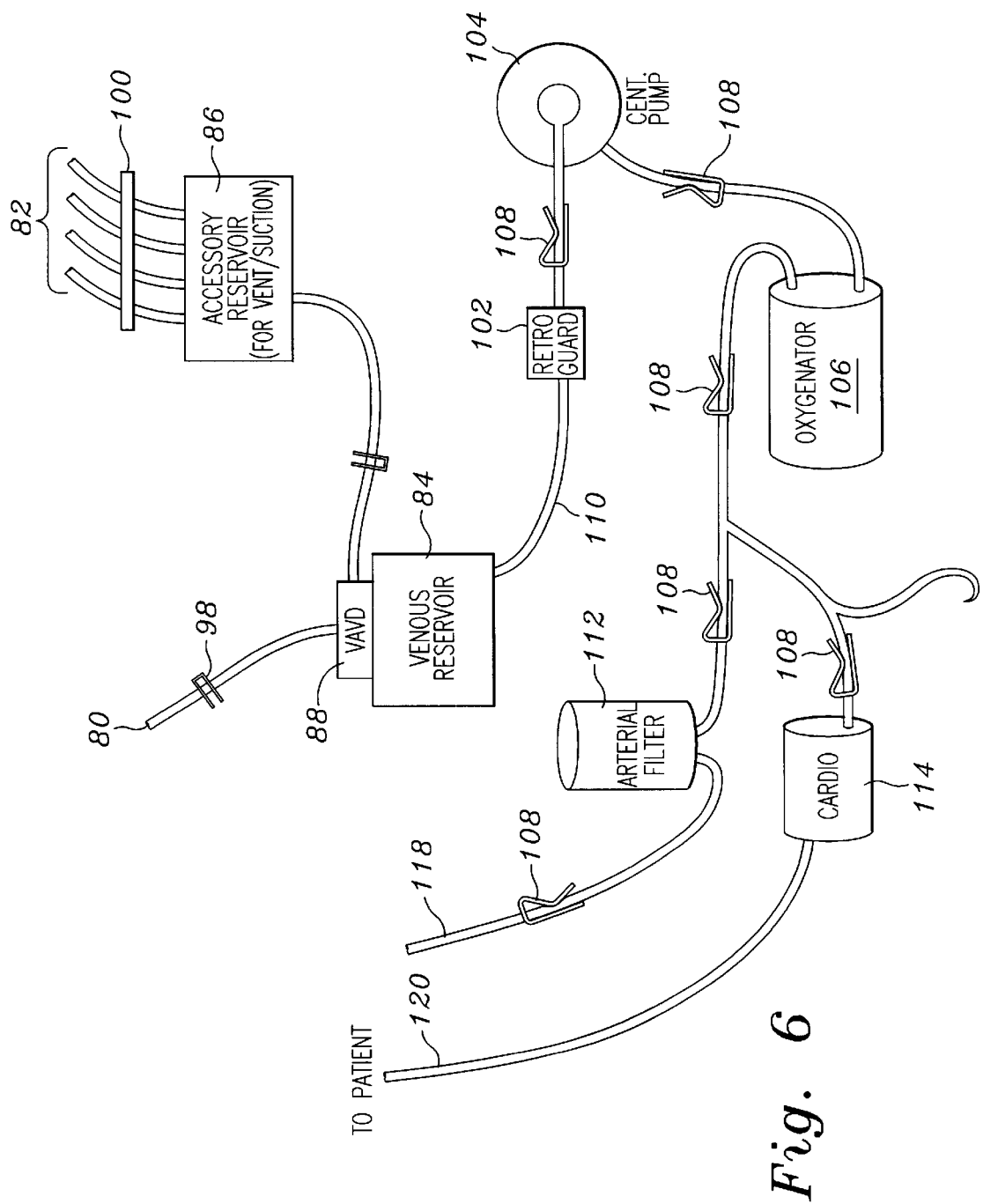
FIG. 6 is a schematic view of various components and connecting tubing of a CPB circuit.
Figure 7:
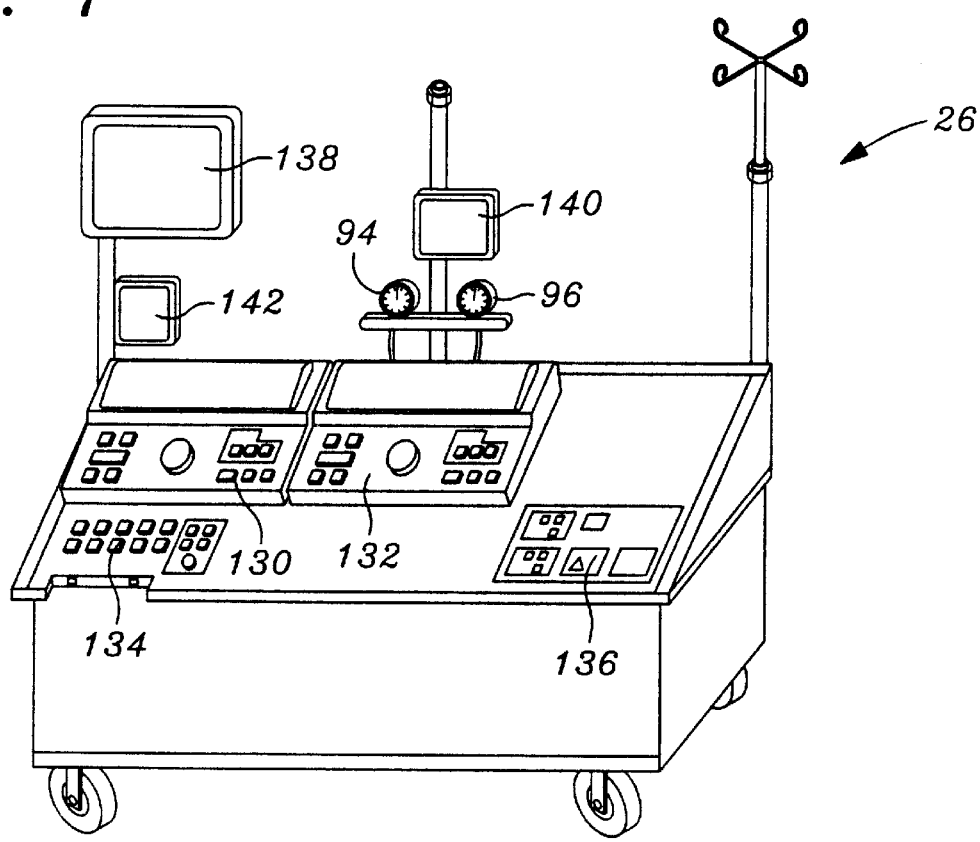
FIG. 7 is a perspective view of a workstation used in the system of FIG. 1.

With reference now to FIGS. 1 and 6, an exemplary embodiment of a bypass circuit 24 for use with the chassis 22 will be described. As seen in FIG. 1, the inlets into the bypass circuit 24 include the venous drainage line 80 and additional suction and vent lines 82. These lines 80 and 82 bring blood from the patient into a venous reservoir 84 and a cardiotomy reservoir 86. The drainage from the patient is assisted by least one vacuum source 88 (FIG. 6). In the embodiment of FIG. 1, the vacuum source has vacuum lines 90 and 92 connected to the respective reservoirs to generate the desired pressure differential. The vacuum from each line 90 and 92 is regulated by vacuum regulators 94 and 96 (FIGS. 1 and 7).

Occluders 98 and 100 provided on the drainage lines 80 and 82 control flow from the patient. These occluders 98, 100 are preferably adjustable electronic occluders which control flow where needed in both positive and negative pressure areas of the system 20. For example, a positive pressure occluder controls cardioplegia blood flow while a negative pressure control point would regulate the aortic root (AO root) vent system. The use of these vacuum sources advantageously reduces the need for a centrifugal pump on the venous line and eliminates the need for three (3) roller pumps used in conventional pump systems for drainage of venting systems and cardiotomy suction. The vacuum sources do not have as much mechanical interaction with the blood and thus will reduce hemolysis over conventional systems.

As illustrated in FIG. 6, a retroguard valve 102 located between the vacuum-assisted venous reservoir 84 and an arterial centrifugal pump 104 (or as seen at 403 in FIG. 13) isolates the negative pressure in the venous reservoir from an oxygenator 106. A plurality of quick-disconnect devices 108 located along the tubing 110 allows for exchange of bypass circuit components should one of them fail. The tubing is typically between about 3/16 inches and 1/2 inches in diameter and made from PVC or a polytetrafluoroethylene (PTFE) equivalent. The quick-disconnect devices 108 are optionally straight connectors with ribs or barbs on each side with a positive locking/unlocking mechanism enabling the device to be broken into its male and female components. A sealing O-ring is typically an integral part of the connection between male and female components. The devices 108 may also be viewed as adaptive hardware which allows the present invention to be used with currently existing bypass equipment and pump hardware.

Blood exiting the oxygenator 106 may then flow to both an arterial filter 112 and a cardioplegia heat exchanger 114 for delivery back to the patient. And optional cardioplegia pump 116 (FIG. 3) may also be installed to facilitate blood delivery. Typically, an arterial line 118 and cardioplegia delivery line 120 return blood back to the patient.

A bypass circuit 24 of the present invention performs well at higher perfuision pressures generated during some minimally invasive surgical procedures. Antegrade cardioplegia flow effected by delivery of solutions through the coronary arteries is determined to some degree by arterial line pressure. For example, arterial line pressure of 320 mmHg has an antegrade cardioplegia flow of 270 ml/min, with a 90 mmHg aortic root pressure. Similarly, arterial line pressure of 150 mmHg has an antegrade cardioplegia flow of 65 ml/min, with a 100 mmHg aortic root pressure. For patients who exhibit great flow rates at the lower end of arterial line pressures, bypass circuit pressure could be artificially and temporarily increased during antegrade cardioplegia administration to optimize cardioplegia flow. Retrograde cardioplegia flow, with maximum flows in excess of 300 cc/min, seems unaffected by the arterial line pressure.

Optionally, the cardiotomy reservoir 86, such as a Bentley CATR-3500 reservoir manufactured by Baxter International Inc., can be used for cardiotomy return and cell salvage, connected and intermittently drained to either the venous reservoir or the cell saver depending on the quality of the contents. At the end of the procedure, the cardiotomy reservoir 86 can be utilized as a chest drainage reservoir in the post-operative setting. This eliminates the current practice of acquiring a separate chest tube drainage reservoir at additional expense to the procedure. All reservoirs will preferably utilize a pressure relief system, providing both positive and negative pressure limits.

Figure 8:
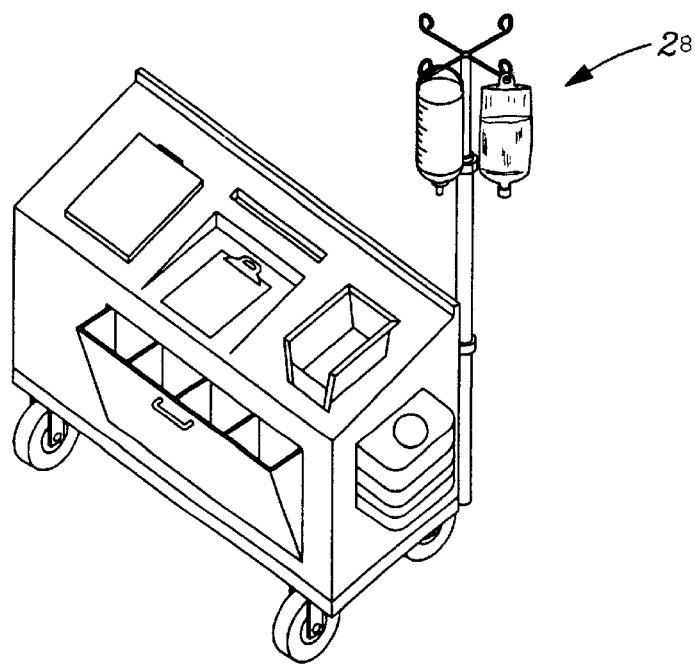
FIG. 8 is a perspective view of another workstation used in the system of FIG. 1.
Figure 10:
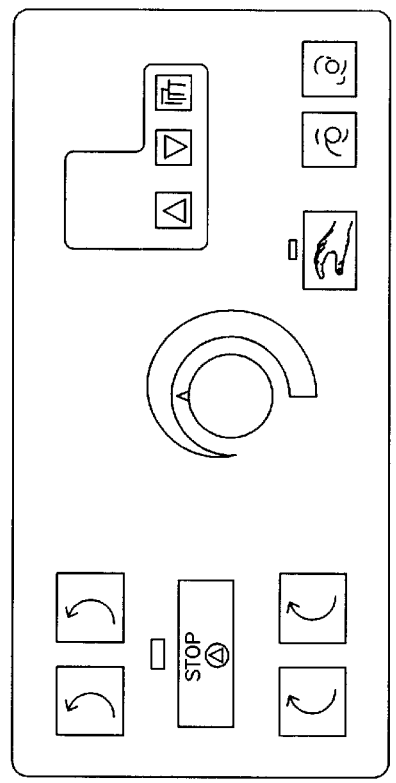
FIGS. 9–12 are plan views of various control panels of the workstation shown in FIG. 7.
Figure 9:
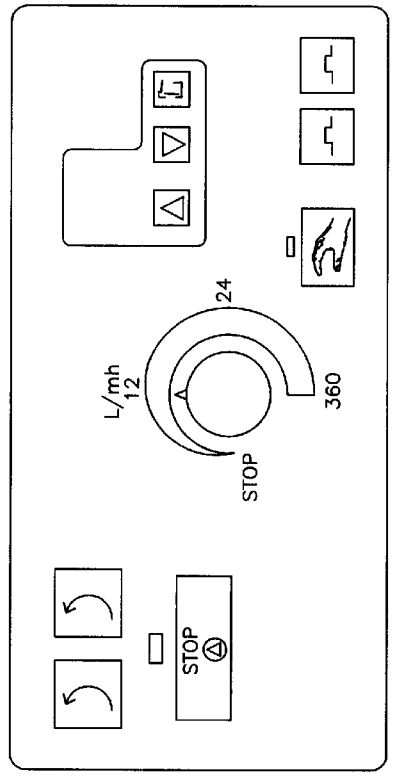
Figure 12:
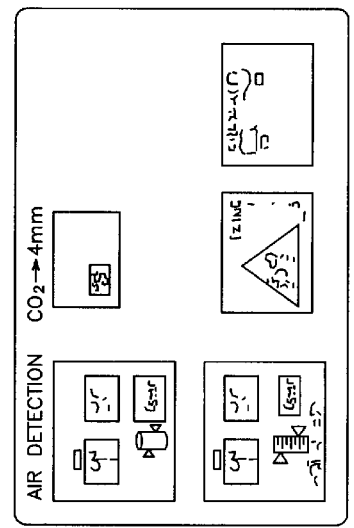
Figure 11:
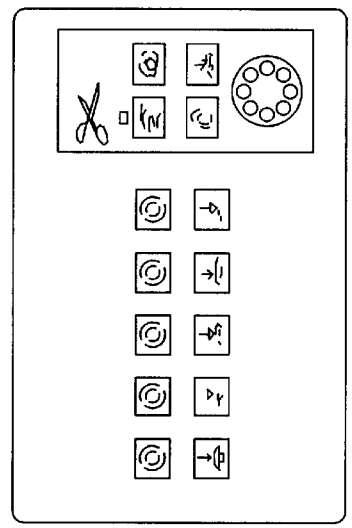

FIGS. 7 and 8 show preferred embodiments of the workstations 26 and 28. Workstation 26 contains a console 130 for arterial, centrifugal pump control and a console 132 for cardioplegia roller pump or centrifugal pump control if desired. Left console panel 134 controls suction and vent occluder controls, and venous line variable occluder controls. Right console panel 136 provides safety features such as level detection, alarm detection, CO2 flush control, and power source-battery indicator. Perfusion information is displayed on monitor 138. T.E.E. and DLP negative pressure transducer information are displayed on monitors 140 and 142, respectively. Vacuum regulators 94 and 96 regulate venous return and cardiotomy suction and vents, respectively. Sharps containers and the like are on workstation 28 (FIG. 8). FIGS. 9–12 illustrate the control panels discussed above.

With reference now to FIGS. 13–18, one preferred embodiment of the present invention is disclosed. As mentioned above, the support device can be formed of molded plastic, a wire grid, a rigid board with cutouts, or any number of constructions. In a preferred embodiment, a lightweight, flexible polymer sheet is used, with the various openings for surgical components formed by cutouts in the sheet. There are a number of benefits derived from using a polymer sheet, including a low manufacturing cost, low weight, ease-of-use, and design flexibility. In one embodiment shown, the sheet is substantially planar with all the components been arrayed on one side. This provides the additional advantage of permitting the sheet to be assembled with the components facing one way or the other. In other words, the sheet is reversible to enable the components to be displayed in either a right- or left-handed orientation, from the perspective of the perfusionist.

In addition, those of skill in the art will understand that the planar configuration is only one possible construction. Alternatively, a planar sheet may be bent into three-dimensional shapes, such as cylinders, for supporting and displaying surgical components to face in different directions.

Figure 13:
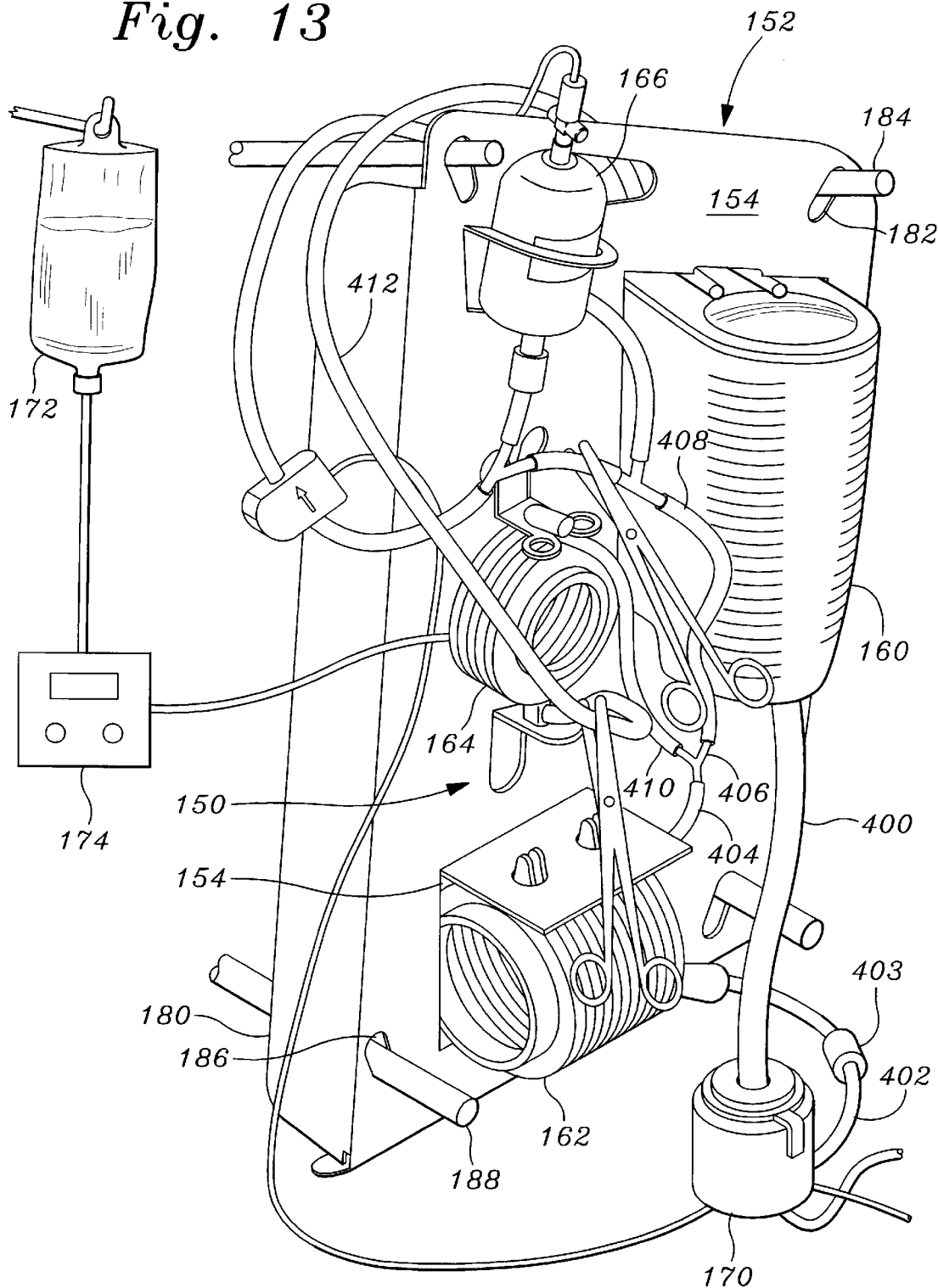
FIG. 13 is a front perspective view of a cardiopulmonary bypass circuit supported and displayed by a further embodiment of the support device of the present invention including a flexible, planar body.

A cardiopulmonary bypass circuit 150 is shown in FIG. 13 supported and displayed on a component support chassis 152. The chassis 152 is formed of sheet material defining a planar body 154 having a plurality of openings, such as opening 156, for receiving the various bypass circuit components. The particular bypass circuit 150 shown includes a reservoir 160, an oxygenator 162, a cardioplegia heat exchanger 164, and an arterial filter 166. In the operating room, the cardiopulmonary bypass circuit 150 will be connected to a blood pumping system, such as a centrifugal pump 170 (or roller pump system as previously shown). In addition, a source of cardioplegia solution 172 will be connected to supply solution to the heat exchanger 164 via an intravenous pumping/metering device 174. Some of the tubing necessary for bypass is not shown in FIG. 13, such as the venous and cardiotomy drainage lines that would connect to the upper portion of the reservoir 160. Likewise, other components such as a separate cardiotomy reservoir may be present and supported on the chassis 152. The venous drainage may be by gravity, with the reservoir 160 positioned below the level of the patient, or may be vacuum-assisted, in which case the height of the reservoir 160 relative to the patient is not as important.

The component support chassis 152 comprises the planar body 154 previously mentioned, and a plurality of bent outer flanges, such as side flange 180, for stability. The assembled configuration is somewhat like a vertically-oriented tray. The flanges may be bent so that the tray is rearwardly- or forwardly-facing, depending on what side the components are displayed. A pair of angled slots 182 in the upper corners of the planar body 154 receive horizontal support rods 184. The pair of angled slots 182 are spaced apart such that the support rods 184 are forced apart slightly after the chassis 152 is suspended therefrom. This helps maintain the chassis 152 in place through the friction between the slots 182 and support rods 184. A lower pair of apertures 186, which may also be angled slots, is provided in the planar body 154 and receives a corresponding pair of horizontal support rods 188.

Figure 14:
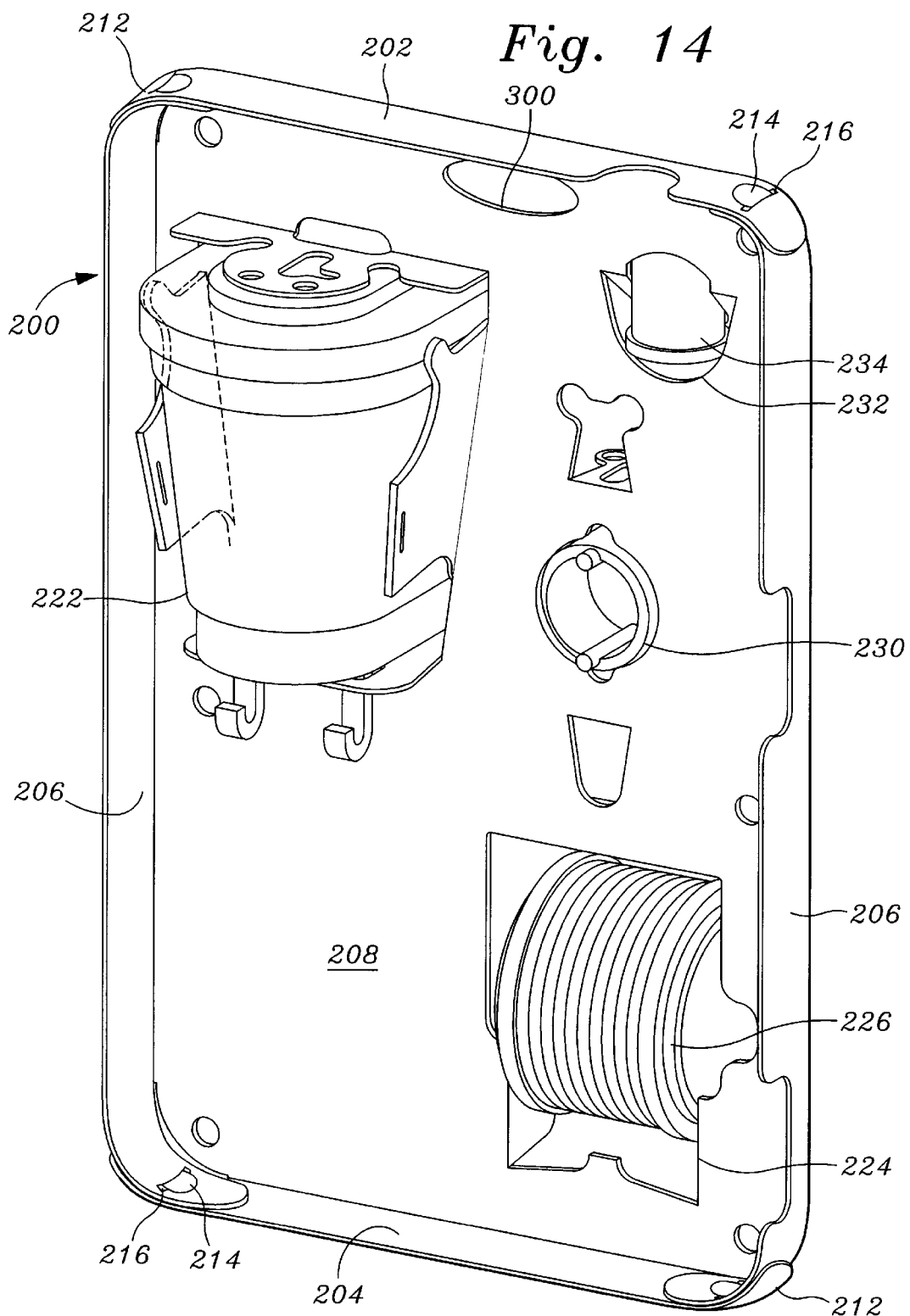
FIG. 14 is a rear perspective view of another embodiment of the support device including a flexible, planar body showing a number of cardiopulmonary bypass circuit components received in openings therein.
Figure 15:
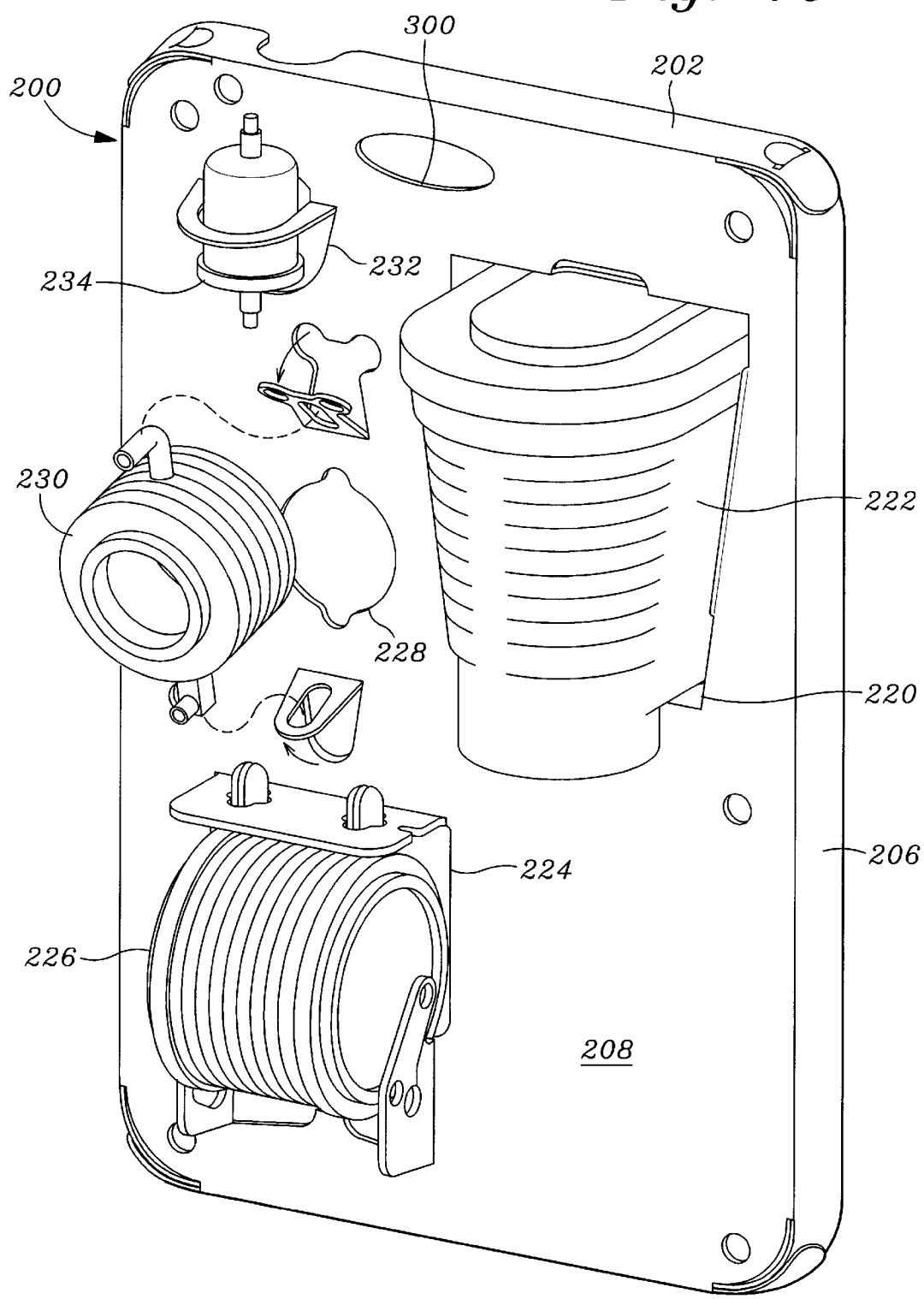
FIG. 15 is a front perspective view of the support device of FIG. 14 showing the bypass circuit components without interconnecting tubes.

FIGS. 14 and 15 are front and rear perspective views, respectively, of another embodiment of the component support chassis 200 of the present invention. The chassis 200 is in many respects similar to the chassis 152 seen in FIG. 13, although the reader will see that the chassis 200 also includes an upper flange 202. The chassis 200 further includes a lower flange 204 and pair of side flanges 206 bent rearwardly from a planar body 208 along lines 210. The flanges are coupled at their adjacent ends to form corners 212 of the chassis 200. More specifically, a coupling tab 214 is received in a coupling slot 216 at each corner 212. This box-shaped construction renders the assembled component support chassis 200 relatively rigid, although it is desirably constructed of relatively thin and flexible polymer sheet material.

A preferred material for the component support chassis 200 seen in FIGS. 13–15 is sheet extruded high-density polyethylene. The material is desirably formed to a thickness of between 1.02–2.29 mm (0.040–0.090 in), and more preferably to a thickness of about 1.57 mm (0.062 in). If the material is formed too thick, bending of various tabs and flanges might cause cracking, while the material must be thick enough to support the various surgical components when filled with fluids. Other materials may also be used, including Teflon®, Delrin®, or other non-brittle, non-abrasive polymer. Non-brittle materials enable the tabs to be repeatedly bent without cracking. The surgical components are typically constructed of a polycarbonate, and the chassis should be non-abrasive to avoid scuffing or possible forming particulates from vibratory contact with the components.

As with the earlier embodiment, the component support chassis 200 includes a plurality of openings for receiving and supporting various surgical components. With particular reference to FIGS. 14–15, the chassis 200 includes an opening 220 formed in upper right portion thereof (as seen from the front in FIG. 15) that receives a reservoir 222. A second opening 224 receives an oxygenator 226. A third opening 228 receives a cardioplegia heat exchanger 230, and a fourth opening 232 receives an arterial filter 234. Each of these openings receives at least a portion of the corresponding surgical component and, in conjunction with a plurality of retainers formed adjacent the openings, supports the surgical components even when full.

As mentioned, a plurality of retainers are provided in the chassis 200 adjacent the aforementioned openings to help support the surgical components. In a preferred embodiment, the retainers comprise tabs formed in specific shapes for mating with the corresponding architecture of each of the surgical components. The tabs are desirably formed by cut lines in the planar body 208 and are designed to bend outward from the plane of the planar body and releasably couple with the surgical components. Therefore, those of skill in the art will recognize that the preferred polymer sheet material enables a plurality of tabs to be cut therein and be bent along living hinge lines. However, the invention should not be construed as limited to tabs pivoted about living hinges. That is, other arrangements which rely on separate tabs hingedly coupled to the chassis 200 are contemplated. Furthermore, the openings themselves may be provided in the polymer sheet, and the surgical components coupled to the chassis 200 by way of straps, hooks, or other such expedients. In short, the illustrated chassis 200 is only one of a number of ways of supporting and displaying interrelated medical components.

Figure 16:
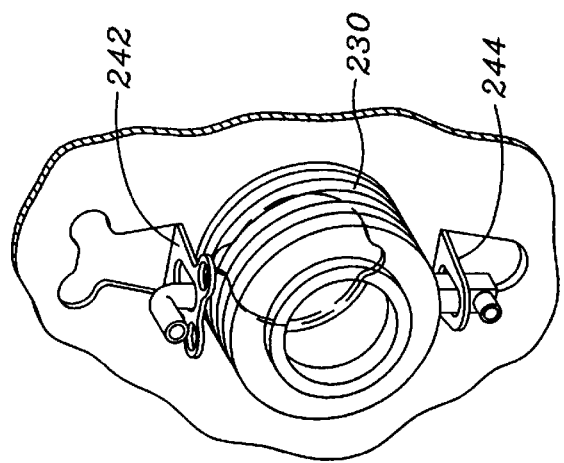
FIG. 16 is an isolated perspective view of FIG. 15 showing a cardioplegia heat exchanger releasably retained by tabs bent out of a planar body of support device.

With reference to the plan view of FIG. 17, in conjunction with the perspective views of FIGS. 14–16, the various tabs for the medical components illustrated will now be described. Beginning at the upper left portion of the planar body 208, an arterial filter tab 240 is formed adjacent the filter opening 232. An upper cardioplegia heat exchanger tab 242 is disposed directly below the filter tab 240. A lower cardioplegia heat exchanger tab 244 is formed opposite the heat exchanger opening 228 from upper tab 242. Just below tab 244 is an upper oxygenator tab 250 adjacent the oxygenator opening 224. The oxygenator is also held in place by a pair of a lower tabs 252. The right side tab 252 includes an elongated tubing release tab 254 which can be partly separated from the main tab portion along score line 256. Finally, the reservoir 222 is releasably held in place using an upper tab 260, pair of door tabs 262, and a lower tab 264.

A number of the illustrated tabs include small apertures therein for receiving fluid inlet or outlet ports integrally formed with the respective surgical component, or for receiving tubing connected to such ports. In addition, several of the tabs are provided with apertures for receiving rigid mounting flanges provided on the components. For example, upper oxygenator tab 250 includes a pair of apertures 270 for receiving mounting flanges 272 on the oxygenator 226. Finally, some of the tabs include finger holes for grasping and bending the tabs from the plane of the body 208. For example, upper reservoir tab 260 includes finger holes 274 and the upper heat exchanger tab 242 includes a pair of finger holes 280.

The tabs are designed to securely retain each of the components in its respective position on the chassis 220, while permitting easy release. During setup of a cardiopulmonary bypass circuit, for example, the perfusionist often wishes to manipulate various components to facilitate priming and remove air bubbles from within. In one specific example, the upper heat exchanger tab 242 includes the finger holes 280 and an elongated slot 282 for receiving an upper fluid inlet port 284. By tilting the heat exchanger 230 toward the planar body 208 and grasping the finger holes 280, the upper tab 242 can be pivoted toward the planar body, thus releasing the heat exchanger 230 for manipulation. Likewise, as seen in FIG. 15, the tubing release tab 254 can be pulled outward from planar body 280, thus partly separating it along score line 256 from the lower tab 252. The score line terminates in tubing aperture 290, which permits the oxygenator 226 to be lifted free of the chassis 220.

A number of score lines are formed in the planar body 208 to enable various portions to be more easily bent and retain the bent position. So, for example, each of the peripheral flanges bends with respect to the planar body 208 about a score line 292. Likewise, some of the tabs also bend about score lines, such as, for example, all of the tabs for retaining the reservoir 222. Some tabs, however, are designed to flex out from the plane of the planar body 208, but exert a restoring force toward the initial position. The upper and lower cardioplegia heat exchanger tabs 242 and 244, for example, are not scored and are biased back into the plane of the body 208. The arterial filter tab 240 is also not scored. These unscored tabs exert a force on the respective components that helps hold them in place with a minimum of material or interconnections. This minimal retaining structure thus facilitates easy manipulation or change out of components.

It should be noted that the cut lines of some tabs are oriented to prevent any tears from propagating toward one of the component openings. The arterial filter tab 240, for example, has an outer edge 294 that is angled away from the filter opening 232. Not only is the bend region strengthened, but any tear that occurs will be directed away from the opening 232, thus preventing failure of the filter support.

The aforementioned specific features of the tabs are related to the particular surgical components supported and displaying by the chassis 220. In the illustrated embodiment, the components are part of a cardiopulmonary bypass circuit available from Baxter International Inc. Those of skill in the art will recognize that the chassis 200, and the other surgical component support devices of the present invention, can be manufactured to receive and support any components available on the market. Therefore, although certain specific features of the tabs shown in FIGS. 14–16 may be used to support components supplied by different manufacturers, other tab designs are likely and contemplated for other medical circuits.

Figure 17:
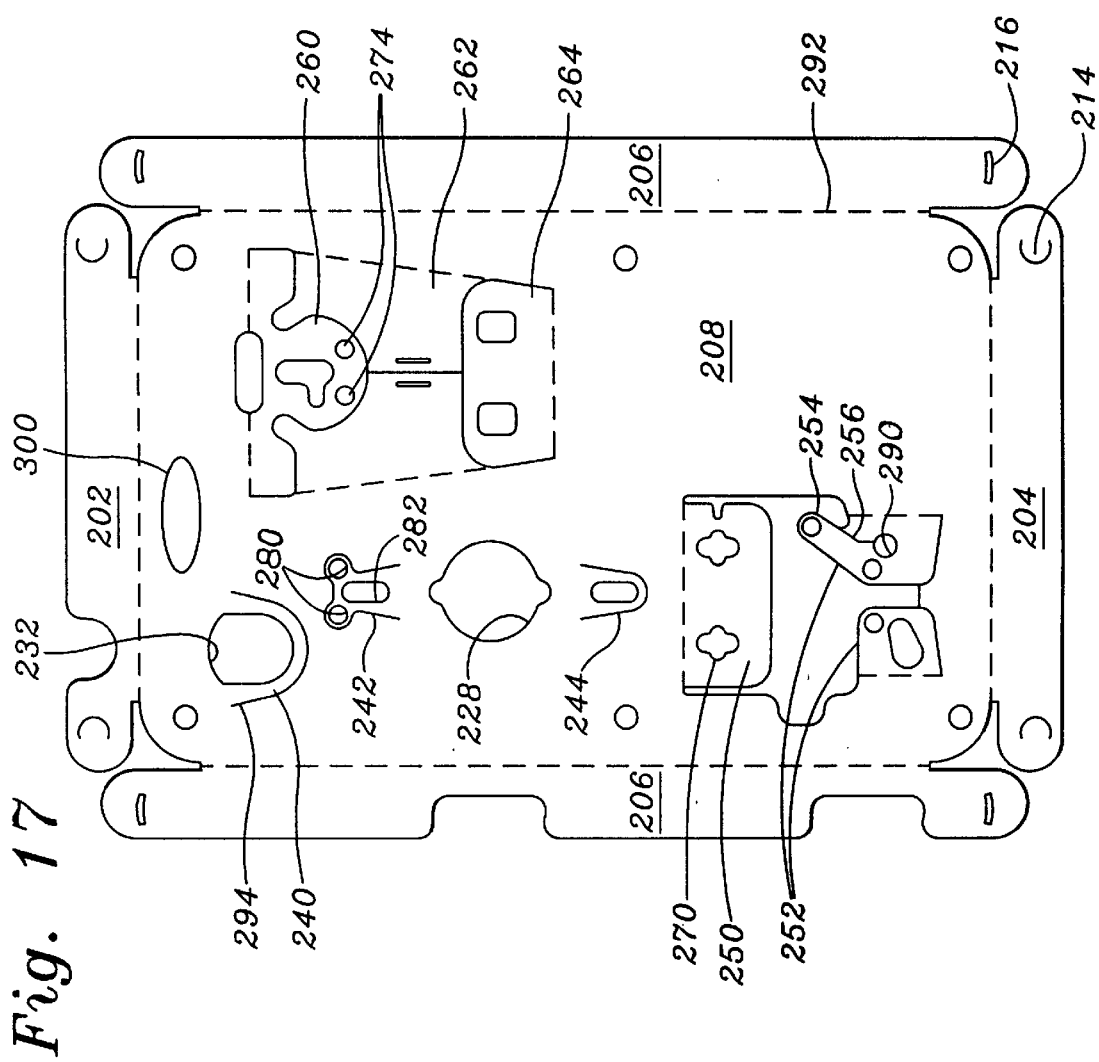
FIG. 17 is a plan view of an unassembled support device, seen assembled in FIGS. 14 and 15.

In this regard, the plan view of FIG. 17 clearly shows the simplified layout of the cut lines used to form the various openings and tabs of the present invention. These cut lines are preferably formed by die cutting the extruded polymer sheet. A die cutting machine comprises a roller having a predetermined knife pattern on its exterior. The sheet is passed underneath the rotating roller which, by downward pressure, cuts the various lines. Alternatively, the knife pattern could be provided on a flat die which is stamped onto the sheet material supported by a table. The particular die is created based on a pattern of the cut lines stored in a computer memory. Therefore, those of skill in the art will understand that it is a relatively simple procedure, using computer-aided drafting technology, to customize the various openings and tabs for an infinite number of medical circuits, which information is then used to form the appropriate cutting die. The dies themselves are relatively inexpensive, on the order of about $1000, and thus in conjunction with the inexpensive sheet material, the present invention enables a manufacturer to rapidly set up and produce a variety of medical component support devices in accordance with the present invention.

The medical component support chassis seen in FIGS. 13–17 each include an oval-shaped handle 300 at an upper central location. The handles 300 are preferably oval-shaped to reduce stress on the fingers. The assembled circuit mounted on the chassis, as best seen in FIG. 15 without accompanying tubing lengths, is packaged and shipped as unit, and may be lifted from the packaging material and mounted in the operating room, such as seen in FIG. 13. The perfusionist then must connect various tubing lengths between the components, and connect the separately provided components, such as the centrifugal pump 170. Once all of the circuit components are connected, the perfusionist then primes the circuit by known methods. Because of the pre-assembled configuration of the circuit, the setup time is greatly reduced. Using separately packaged components, which have to be separately mounted on poles and interconnected, the set up process currently takes between 20–30 minutes. With the pre-assembled circuit of the present invention, the setup process is reduced to about 5 minutes. The shortened setup time can help save lives, and certainly reduces the burden on the perfusionist.

In addition to the shortened setup time, the setup is greatly simplified by the pre-assembled circuit configuration of the present invention. That is, the traditional technique of mounting separate components and connecting them with relatively long lengths of tubing is for the most part replaced by mounting the chassis on the support rods, and connecting the short tubing lengths supplied. Traditionally, the lengths of tubing are typically provided in a custom pack of components depending on the perfusionists preference, and may even be further cut by the perfusionist on site. Of course, the accessories such as the centrifugal pump and cardioplegia solution must still be connected, but the main burden of interconnecting the primary circuit components is removed. To further facilitate ease of connection, the tubing lengths supplied with the components on the chassis may be color-coded with the corresponding component inlet or outlet port.

Moreover, the risk of a sterility break from making numerous connections on site is reduced by the pre-assembled nature of the present system. That is, a number of the connections are already made, with the short lengths of tubing already connected to the components. Essentially, one-half of the component-to-component connections are already made.

The short lengths of tubing pre-connected to various components and shipped with the assembled system are desirable to reduce the chance of contamination, and are sized to precisely extend to the mating component. In this manner, there is no guesswork for the perfusionist in determining the proper tubing lengths. This contributes to the reduced setup time, and also has the additional benefit of reducing the tubing lengths between the components.

One of the primary benefits of the present invention is the reduced prime volume in the cardiopulmonary bypass circuit. As mentioned, pre-connected lengths of tubing are provided on various components in the system to be interconnected with other components at the time of setup. The interconnecting tubing lengths are thus sized just long enough to extend between the components, which are mounted in a predetermined relationship on the chassis, without kinking. This eliminates any excess tubing between components. Furthermore, the compact and portable nature of the chassis-mounted circuit enables the circuit to be moved as unit closer to the operating table. Indeed, the chassis may be mounted on support rods extending from the operating table, which would further reduce the lengths of tubing extending between the circuit and a patient. These features, particularly when used in conjunction with vacuum-assisted venous drainage, can reduce the entire prime volume of a cardiopulmonary bypass circuit to less than 1500 cc, and preferably less than 1000 cc.

Figure 18:
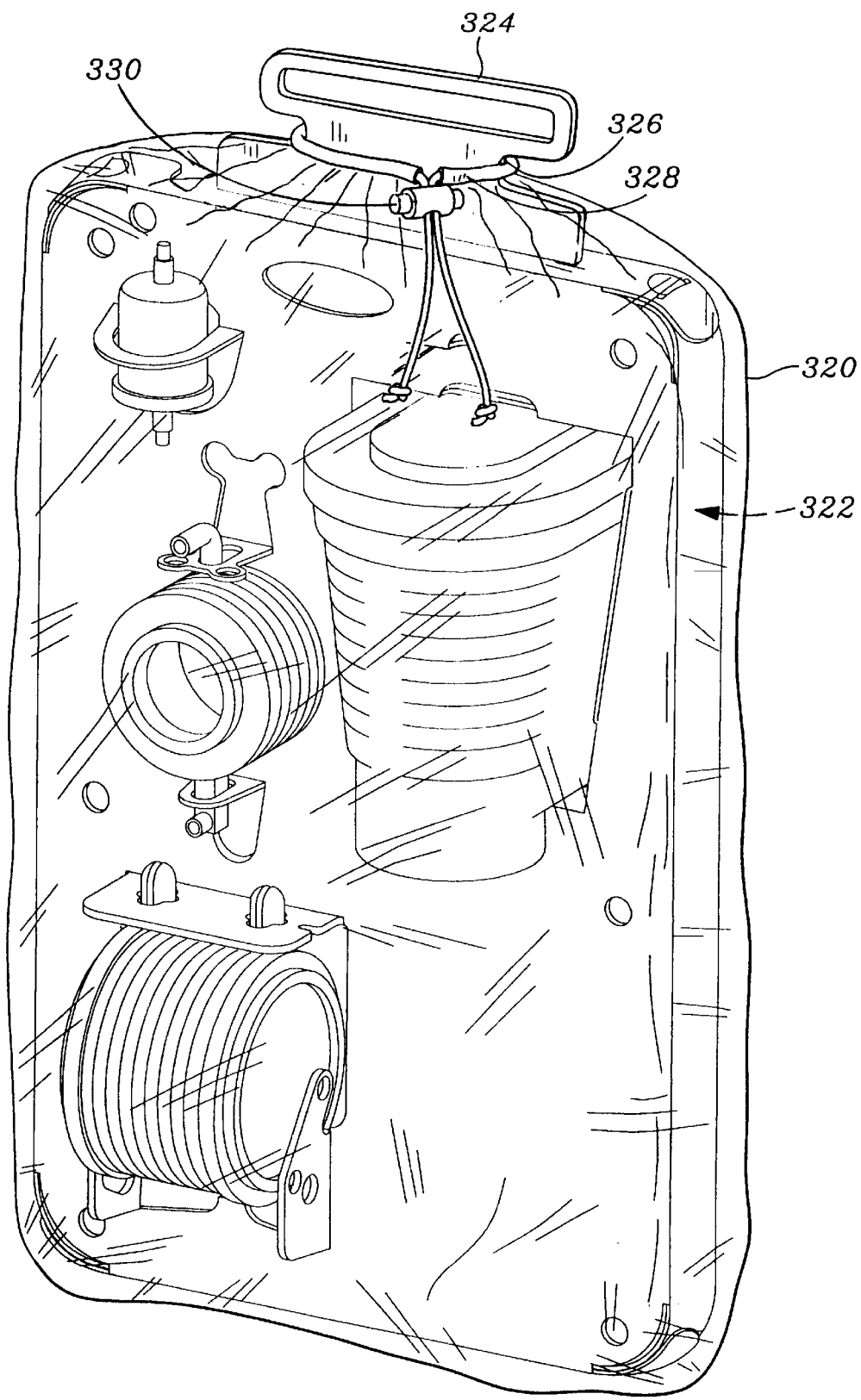
FIG. 18 is a perspective view of cardiopulmonary bypass circuit mounted on the device of the present invention and enclosed within a clean bag for easy disposal.

FIG. 18 illustrates a clean bag 320 encompassing a chassis 322 of the present invention on which a plurality of cardiopulmonary bypass circuit components are mounted. The chassis 322 includes an upper handle 324 having a neck portion 326. The clean bag 320 can be closed around a neck portion 326 via a string 328 and cinch device 330.

The clean bag 320 may be part of the pre-assembled system packaging, and may be reused to dispose of the system after the circuit has performed its function. That is, all of the components in a cardiopulmonary bypass circuit must be disposed of in infectious waste containers. Typically, with separate components, each are separately bagged and placed in a large container to be transported to an infectious waste dumpster in a rear of a hospital. With the chassis 322 of the present invention and clean bag 320, the entire circuit can be disposed of at once. That is, the chassis 322 and circuit are deposited in the clean bag 320, with the handle 324 extending out from the top. The entire assembly can then be transported to the infectious waste dumpster. This system greatly reduces the time and inconvenience in separately packaging and disposing of potentially infectious circuit components.

Pump-less Cardioplegia Delivery

The present invention including a device for supporting a plurality of cardiopulmonary bypass components in close proximity to one another is particularly well-suited to implement pump-less cardioplegia delivery. This is so because of the close arrangement of the components, which minimizes the tubing needed to connect the oxygenator and cardioplegia heat exchanger. However, the principles of pump-less cardioplegia delivery do not depend on the particular arrangement of components, and can be implemented in any bypass system.

Figure 19:
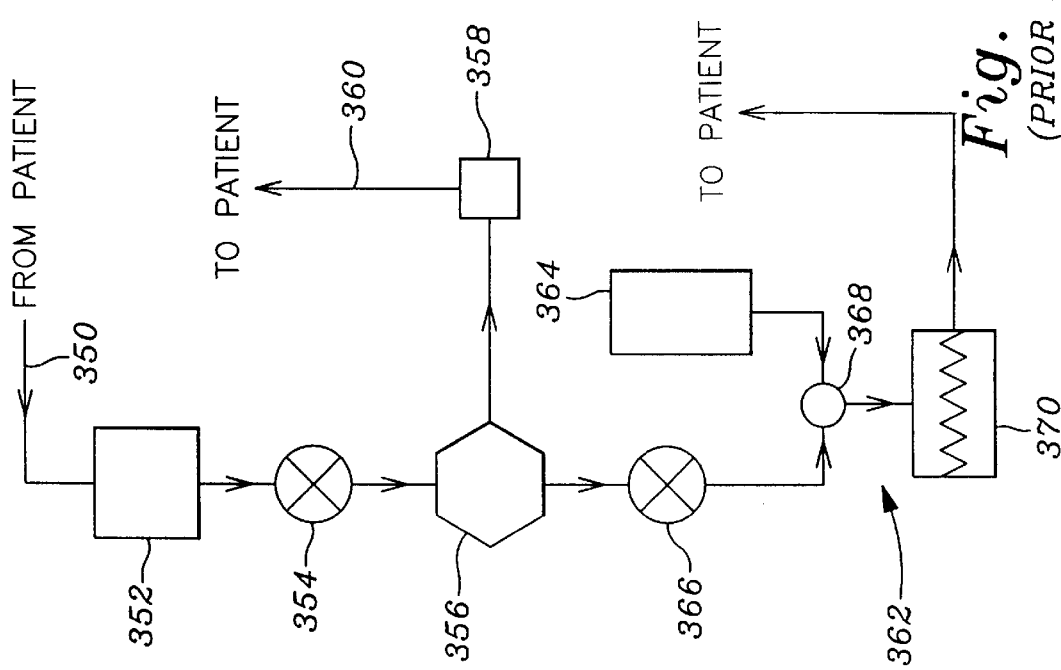
FIG. 19 is a schematic diagram of a prior art CPB circuit with cardioplegia pumping.

With reference to FIG. 19, a schematic cardiopulmonary bypass system of the prior art is shown. A venous input line 350 receives blood from the patient and delivers it to a filtered venous reservoir 352. As mentioned above, there are often a plurality of sucker lines (not shown) positioned to aspirate various fluids and debris from the chest cavity and deliver it to the reservoir 352. Blood that has collected in the reservoir 352 is then impelled by pump 354 through an oxygenator 356 (typically incorporating a heat exchanger) an arterial filter 358, and back to the patient through arterial line 360.

The circuit also includes a cardioplegia delivery system 362 including a cardioplegia fluid supply 364, a second pump 366, a mixer 368, and a cardioplegia heat exchanger 370. Some of the oxygenated blood from oxygenator 356 is impelled by pump 366 to mixer 368 to be combined with cardioplegia solution from supply 364. This mixed blood and cardioplegia solution is then directed through the cardioplegia heat exchanger 370 and delivered by a ¼ inch or smaller cardioplegia delivery tubing to either a antegrade cardioplegia catheter or a retrograde cardioplegia catheter (not shown) for myocardial protection once the heart is isolated from normal blood circulation. The cardioplegia heat exchanger 370 acts as a bubble trap. The pumps 354 and 366 are typically either occlusive-type roller pumps, or in some cases centrifugal pumps with valves preventing backflow. The pump 366 and the mixer 368, and additional tubing required for them, cause associated complement activation and potential hemolysis to the system.

Figure 20:
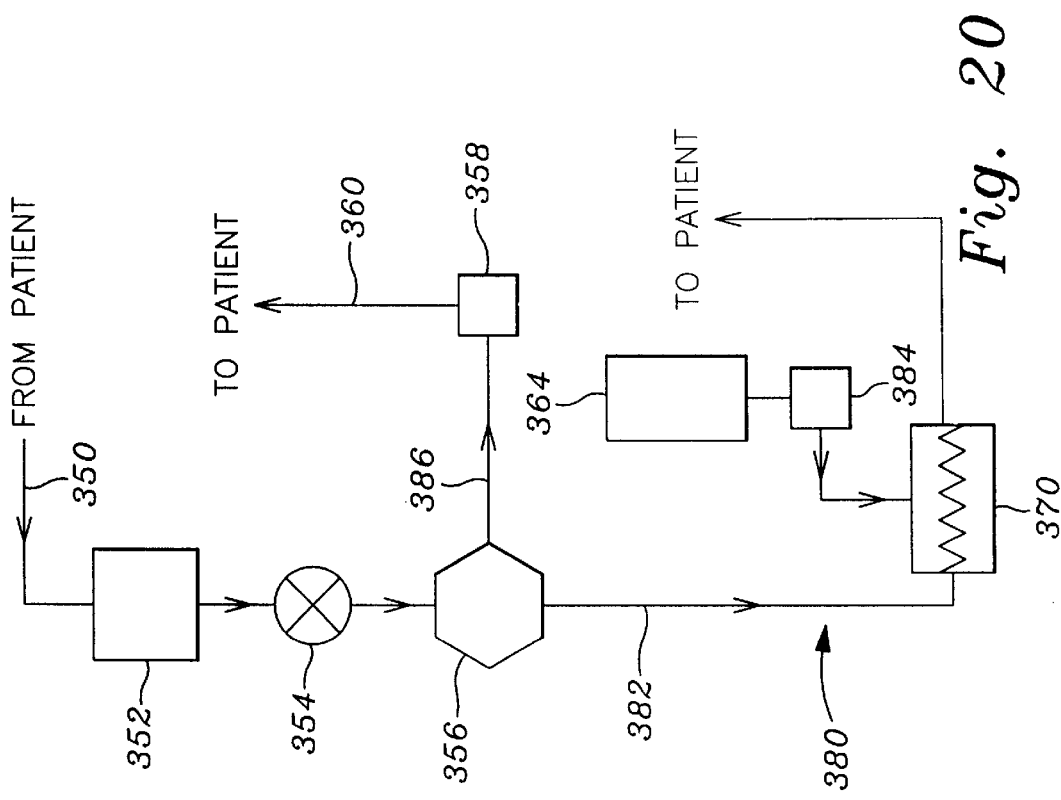
FIG. 20 is a schematic diagram of a CPB circuit of the present invention with pump-less cardioplegia delivery.

FIG. 20 illustrates an improved pump-less cardioplegia delivery system 380 of the present invention. Some of the components of the circuit shown identical to those in FIG. 19, and will be so numbered. As before, fluid pressure generated by pump 354 impels blood through oxygenator 356, filter 358, and back to the patient through arterial line 360. Delivery line 382 connects a second outlet of the oxygenator 356 directly with cardioplegia heat exchanger 370, without an additional pump. The cardioplegia solution from supply 364 passes through an intravenous infusion pump 384 before being directed to the cardioplegia heat exchanger 370. The cardioplegia solution and oxygenated blood mix within the heat exchanger 370. Fluid pressure generated by pump 354 is utilized to impel blood and cardioplegia solution through heat exchanger 370, and through ¼ inch or smaller cardioplegia delivery tubing to the patient's isolated heart via a cardioplegia catheter (not shown). This arrangement, therefore, eliminates the need for a second roller or centrifugal pump, such as pump 366 in FIG. 19, and separate mixer 368.

Tests have shown that adequate flow through the cardioplegia heat exchanger 370 is obtained with an arterial line 360 pressures of as low as 100 mmHg. The blood pressure generated by pump 354 is scavenged from the primary return line 386 and utilized to impel cardioplegia solution through the heat exchanger 370 and through the tubing to the patient.

An alternative to delivering the cardioplegia solution to the cardioplegia heat exchanger 370 would be to add the cardioplegia solution at the antegrade or retrograde catheter utilizing an IMED style pump and a ¼ inch or smaller tubing, with IV size tubing integrally attached to the ¼ inch or smaller tubing coming from the cardioplegia heat exchanger.

The adequacy of cardioplegia solution flow depends to some extent on the method of cardioplegia catheter insertion. That is, the cardioplegia catheter can be inserted retrograde, or antegrade. Retrograde insertion involves catheterizing the coronary sinus with a specific type of cardioplegia catheter. Antegrade insertion involves catheterizing the aortic root or coronary ostia with a different type of cardioplegia catheter. The types of cardioplegia catheters and insertion methods are well known in the art.

The cardioplegia delivery pressure in the pump-less cardioplegia system of the present invention may depend on the arterial line pressure. Cardioplegia flow in retrograde insertion is sufficient with most arterial line pressures provided by the pump 354. If the arterial cannula is inserted antegrade, on the other hand, cardioplegia flow will depend to a much greater degree on arterial line pressure. The following table illustrates the relationship between arterial line pressure, antegrade cardioplegia flow, and aortic root pressure using the system shown in FIG. 20, as tested in an animal model.

TABLE I

Antegrade Cardioplegia Flow vs. Arterial Line Pressure

| Arterial Line Pressure | Antegrade Cardioplegia Flow | Aortic Root Pressure |
|---|---|---|
| 320 mmHg | 270 ml/min | 90 mmHg |
| 150 mmHg | 65 ml/min | 100 mmHg |

The system shown schematically in FIG. 20 is also illustrated in perspective in FIG. 13. Blood from the reservoir 160 passes through tubing 400 into centrifugal pump 170, and then through tubing 402 to oxygenator 162. A retroguard valve 403 is provided in tubing 402 to prevent backflow or regurgitation to the centrifugal pump 170. Oxygenator outlet tubing 404 is connected to a Y-junction 406 that branches the flow into tubing 408 and tubing 410. Tubing 408 extends to arterial filter 166, and from there back to the patient. Tubing 410 connects to an input of cardioplegia heat exchanger 164. Cardioplegia solution from supply 172 is also directed to cardioplegia exchanger 164 through intravenous infusion pump 174. The oxygenated blood passing through tubing 410 mixes with the cardioplegia solution within the heat exchanger 164, and is then returned to patient by tubing 412 in communication with a cardioplegia catheter (not shown).

While the foregoing is a complete description of the preferred embodiments of the invention, various alternatives, modifications, and equivalents may be used. For example, a cardioplegia pump may be eliminated by using arterial line pressure and a variable occlusion clamp powered by solenoids and the like to clamp on the blood line and directly inject the arresting agents by IMED style IV pump, thus eliminating the need for a 4:1 tubing set. The chassis may also be integrated directly into the operating table or some portion of the control workstation. Certain elements such as the oxygenator can be combined with an internal hemoconcentrator to reduce the number of individual bypass components. It will be obvious that certain other modifications may be practiced within the scope of the appended claims.

What is claimed is:

1. A support device for an extracorporeal blood circuit in which a blood reservoir, an oxygenator, a blood filter and a plurality of tubing sections are in fluid communication with each other, said support device comprising:
    a chassis having a planar surface;
    means for removably mounting and supporting the blood reservoir, oxygenator and blood filter in close proximity on the chassis; and,
    a series of channels formed in the chassis, said channels sized to receive and protect the tubing sections, wherein the channels are defined by the absence of material in the chassis and parallel to the planer surface of the chassis.

2. The support device of claim 1, when the support means comprises a plurality of openings in the chassis.

3. The support device of claim 2, wherein the chassis is formed of a polymer sheet and the openings are cut therein.

4. The support device of claim 3, further including a plurality of tabs formed by cuts in the polymer sheet, the tabs being bendable from the plane of the polymer sheet and being adapted to releasably retain the extracorporeal blood circuit components.

5. The support device of claim 4, wherein one or more of the cuts are directed away from the openings so that any tears that may occur between the tabs and the polymer sheet are propagated away from the openings.

6. The support device of claim 2, wherein the chassis comprises a generally planar body and is reversible so that the blood reservoir, oxygenator, and blood filter may be supported and displayed in the openings from either side of the planar body.

7. The support device of claim 1, wherein the chassis is rigid.

8. The support device of claim 1, wherein the chassis is planar.

9. The support device of claim 1, wherein the chassis is flexible.

10. The support device of claim 1, wherein the chassis is generally planar.

11. The support device of claim 1, wherein the chassis is formed of a polymer.

12. The support device of claim 11, wherein the polymer is non-brittle and non-abrasive.

13. The support device of claim 1 wherein the support means comprises a plurality of retainers.

14. The support device of claim 13, wherein the retainers comprise straps.

15. The support device of claim 13, wherein the retainers comprise hooks.

16. The support device of claim 13, wherein the retainers comprise hook and loop fasteners.

17. The support device of claim 13, wherein the retainers comprise tabs formed in the chassis.

18. The support device of claim 17, wherein the tabs are flexible and may be bent away from the chassis.

19. The support device of claim 18, wherein the chassis comprises a planar body, and wherein the tabs are formed by cuts in the planar body that are bendable from the plane of the planar body about living hinges and are adapted to releasably retain the extracorporeal blood circuit components.

20. The support device of claim 1, wherein the support means comprises adhesive bonds.

21. The support device of claim 1, wherein the extracorporeal blood circuit components are integrally formed into the chassis.

22. The support device of claim 1, wherein the chassis comprises a wire grid and the extracorporeal blood circuit components are supported by the wire grid using suitable retainers.

23. The support device of claim 1 wherein the support means and the channels are arranged in sufficiently close proximity that the prime volume for the entire extracorporeal blood circuit is less than 1500 cubic centimeters.

24. The support device of claim 23 wherein the support means and the channels are arranged in sufficiently close proximity that the prime volume for the entire extracorporeal blood circuit is less than 1000 cubic centimeters.

* * * * *